(12) United States Patent
Fargahi

(10) Patent No.: US 8,870,855 B2
(45) Date of Patent: Oct. 28, 2014

(54) RELEASE MECHANISM FOR RELEASING A MEDICAL IMPLANT FROM A CATHETER, AND CATHETER HAVING A RELEASE MECHANISM

(71) Applicant: Biotronik AG, Buelach (CH)

(72) Inventor: Amir Fargahi, Buelach (CH)

(73) Assignee: Biotronik AG, Buelach (CH)

( * ) Notice: Subject to any disclaimer, the term of this patent is extended or adjusted under 35 U.S.C. 154(b) by 153 days.

(21) Appl. No.: 13/705,051

(22) Filed: Dec. 4, 2012

(65) Prior Publication Data

US 2013/0150829 A1    Jun. 13, 2013

Related U.S. Application Data

(60) Provisional application No. 61/569,299, filed on Dec. 12, 2011.

(51) Int. Cl.
| | | |
|---|---|---|
| A61B 17/00 | (2006.01) | |
| A61F 2/966 | (2013.01) | |
| A61F 2/95 | (2013.01) | |
| A61B 17/12 | (2006.01) | |

(52) U.S. Cl.
CPC ......... *A61B 17/00* (2013.01); *A61F 2002/9517* (2013.01); *A61F 2230/0019* (2013.01); *A61B 2017/00623* (2013.01); *A61F 2220/0091* (2013.01); *A61F 2/966* (2013.01); *A61B 2017/1205* (2013.01)
USPC ........ 606/1; 600/16; 600/17; 604/13; 604/16; 606/16; 606/19; 606/108; 606/153; 607/11; 607/16; 623/1.11

(58) Field of Classification Search
CPC ......... A61N 1/362; A61N 1/00; A61B 18/18; A61B 11/00; A61B 17/08; A61F 2/06; A61F 13/20
USPC ................ 606/1, 99, 206, 16, 19, 108, 153; 604/47, 13, 16; 623/1.11; 254/126; 600/16, 17; 607/11, 16
See application file for complete search history.

(56) References Cited

U.S. PATENT DOCUMENTS

| | | | |
|---|---|---|---|
| 5,192,297 A | * | 3/1993 | Hull ............................. 623/1.11 |
| 5,601,568 A | | 2/1997 | Chevillon et al. |

(Continued)

FOREIGN PATENT DOCUMENTS

WO    WO2011094527 A1    8/2011

OTHER PUBLICATIONS

European Search Report for 12192569.7, Aug. 11, 2013.

*Primary Examiner* — William Thomson
*Assistant Examiner* — Victor Shapiro
(74) *Attorney, Agent, or Firm* — Wagenknecht IP Law Group PC

(57) ABSTRACT

A release mechanism (100, 100*a*) for releasing a medical implant (105) from an insertion device (110), comprising a body (10) having a proximal end (12) and a distal end (14), wherein between the proximal end and the distal end (12, 14) an actuator (16, 16*a*) is provided, wherein for generating a selective relative displacement between the first and second insertion elements (72; 74) of the insertion device (110), the actuator (16, 16*a*) has a first and at least a second direction of motion (18; 20), wherein in the first direction of motion (18), the first and second insertion elements (72; 74) can be displaced relative to one another in the longitudinal direction (18), and wherein in the at least second direction of motion (20), the actuator (16, 16*a*) effects a movement transversely to the longitudinal direction (18).

16 Claims, 5 Drawing Sheets

(56) References Cited

U.S. PATENT DOCUMENTS

| | | | | |
|---|---|---|---|---|
| 6,066,174 | A * | 5/2000 | Farris | 606/206 |
| 6,607,181 | B2 * | 8/2003 | Garceau | 254/126 |
| 8,029,458 | B2 * | 10/2011 | Cherif-Cheikh et al. | 604/47 |
| 8,123,757 | B2 * | 2/2012 | Zalenski et al. | 606/99 |
| 2002/0004663 | A1 | 1/2002 | Gittings et al. | |
| 2002/0120277 | A1 | 8/2002 | Hauschild et al. | |
| 2003/0028236 | A1 | 2/2003 | Gillick et al. | |
| 2003/0173076 | A1 * | 9/2003 | Sheiretov et al. | 166/241.1 |
| 2003/0225445 | A1 | 12/2003 | Derus et al. | |
| 2007/0118201 | A1 | 5/2007 | Pappas et al. | |
| 2009/0318928 | A1 * | 12/2009 | Purcell et al. | 606/99 |

* cited by examiner

RELEASE MECHANISM FOR RELEASING A MEDICAL IMPLANT FROM A CATHETER, AND CATHETER HAVING A RELEASE MECHANISM

CROSS REFERENCE TO RELATED APPLICATIONS

This application claims benefit of priority to U.S. provisional patent application Ser. No. 61/569,299, filed Dec. 12, 2011; the content of which is herein incorporated by reference in its entirety.

TECHNICAL FIELD

The invention relates to a release mechanism for releasing a medical implant from a catheter, and to a catheter having a release mechanism for releasing a medical implant for implantation in an animal and/or human body, according to the preambles of the independent claims.

BACKGROUND

In the field of medicine, the use of implants is common, which are introduced permanently or at least for an extended time period inside an animal and/or human body to fulfill a replacement function. Examples of such implants include cardiac pacemakers, cerebral pacemakers for Parkinson's patients, cardiac implants, cochlear implants, retinal implants, dental implants, joint replacement implants, vascular prostheses and stents.

For insertion into the body, implants are connected to catheters, and they must be able to be precisely positioned at their location of use and released in a specific manner. For this purpose it is known, for example, to release the implant by way of a translational motion.

SUMMARY

The problem addressed by the invention is that of specifying a release mechanism with which a highly precise and selective release of an implant can be implemented.

A further problem that is addressed is that of providing a corresponding insertion device.

A release mechanism for releasing a medical implant from an insertion device is provided, in which the implant can be released by way of a relative displacement between a first and a second insertion element. The release mechanism comprises a body having a proximal end, which is disposed facing an operator when in use, and a distal end, which is distant from the operator when in use, wherein an actuator is provided between the proximal end and the distal end, wherein the actuator has a first and at least a second direction of motion for generating a selective relative displacement between the first and the second insertion element of the insertion device, wherein in the first direction of motion, the first and second insertion elements can be displaced relative to one another in the longitudinal direction, and wherein in the at least second direction of motion, the actuator effects a movement transversely to the longitudinal direction.

With the embodiment according to the invention, a release mechanism can be provided in which strong forces can be easily generated. The degree of force to be exerted by the operator and/or doctor can thereby be minimized in a user-friendly manner. The operator and/or doctor can concentrate on a correct positioning of the implant. The release of the implant thus becomes more precise and more rapid. The actuator also allows the relative displacement to be carried out stably and steadily. All of the above results in a high success rate of implantation.

Within this context, a longitudinal direction is understood as a lengthwise direction, a direction along a longitudinal extension and/or a longitudinal direction of displacement of the insertion device. The first direction of motion is preferably a motion in the longitudinal direction. The term "to effect" is understood as "to generate, cause and/or achieve". Additionally, "provided" is understood as specially equipped and designed. The movements in the first and the at least second direction of motion can be carried out successively and/or preferably simultaneously. The movement transversely to the longitudinal direction is limited in terms of distance by the width of the release mechanism (and has, for example, a range of motion of approximately 25 mm). The actuator is advantageously able to convert a movement transversely to the longitudinal direction into a movement in the longitudinal direction. Preferably, a first component of the actuator moves in the first direction of motion, and a second component of the actuator, which is different from the first component, moves in the at least second direction of motion.

Particularly advantageously, with the at least second direction of motion the actuator effects a movement substantially perpendicular and particularly perpendicular to the longitudinal direction. Thereby, the actuator can particularly implement two movements in two directions of motion without constraint, and/or can be operated in two different directions of motion. Within this context, the phrase "substantially perpendicular" is understood to mean that a deviation in the second direction of motion of up to 30° from the longitudinal direction is still understood as perpendicular.

It is further proposed that the actuator comprises at least one spindle, which is disposed in the direction of the at least second direction of motion, thus said spindle is able to predefine the second direction of motion in a structurally simple manner. The spindle advantageously effects the movement transversely to the longitudinal direction. With this configuration, the movement in the at least second direction of motion can be achieved using simple means. Components of the actuator can preferably be moved along the spindle during displacement in the at least second direction of motion. The actuator advantageously has at least one active element for each of the first and the at least second direction of motion, for the purpose of effecting the relative displacement between the first and second insertion elements of the insertion device. Thereby, the movements in the two directions of motion can be transferred with particular precision and efficiency. The active element can be formed by any element deemed appropriate by a person skilled in the art, such as a gear wheel, toothing, an articulated joint and/or screw threading. It is further advantageous for the active element to comprise at least one articulated joint, whereby the respective displacement in the direction of motion can be carried out particularly steadily and steplessly.

In a further embodiment of the invention, it is proposed that an interaction between the spindle and at least one active element effects the displacement transversely to the longitudinal direction, thereby allowing the movement in the at least second direction of motion to be carried out in a structurally simple manner. Additionally, the movement transversely to the longitudinal direction can thereby be converted to the movement in the longitudinal direction in a simple manner. The interaction between the spindle and the active element can be carried out advantageously by way of a transmission element, such as a threaded element, more particularly, internal threading. This permits a compact and simple construction of the actuator or of the release mechanism.

It is further proposed that at least one guide element is provided, which guides the actuator during the movement thereof, thereby allowing the movements in the two directions of motion to be reliably carried out. The guide element can be formed by any element deemed appropriate by a person skilled in the art, such as an opening, a channel, a groove, a wall, a rod, and/or a bar, for example. The actuator and the guide element can be connected to one another via any type of connection, such as a positive connection, a non-positive connection and/or an adhesive connection. Additionally, any relative positioning of the actuator and the guide element can be provided. The actuator is preferably connected at its proximal end to the guide element. For a stable transfer of relative displacement between the first and second insertion elements, the guide element is connected at least to an insertion element of the insertion device. If the insertion device is a catheter, the relevant insertion element can preferably be an outer shaft of the catheter.

In a preferred embodiment, the guide element is supported on the body, which is formed by a housing of the guide device, or the guide element is supported against the housing in which the actuator is disposed. This allows the guide element, and thus the actuator, to be supported in a particularly stable manner. In addition, the housing can comprise at least one guiding device, such as an opening, or a sliding track. The housing can particularly form a handle for the insertion device, resulting in a compact construction. It can further be advantageous for the actuator to be supported against and/or attached to the housing, preferably at the distal end of said actuator. Thus the actuator is fastened in the housing such that it cannot tilt, thereby allowing inhomogeneous movements to be prevented. As a result, the components cannot become jammed. According to an advantageous embodiment, the guide element can have a through passage for one of the insertion elements. This permits a compact configuration, which stabilizes and protects the insertion element that is passed through. If the insertion device is a catheter, the relevant insertion element can be an inner shaft of the catheter.

A simple operation can advantageously be achieved if at least one active element is coupled to a first actuating element. The first actuating element is preferably embodied as integral with the spindle. Within this context "integral" is understood to mean that the actuating element and the spindle are formed by the same component and/or can be separated from one another only with a loss of functioning of at least one of the components. Components, structural space, assembly complexity and costs can advantageously be saved if the spindle forms the first actuating element. It is further proposed that the first actuating element projects out of a housing in which the actuator is disposed, thereby enabling an easy and controlled operability of the release mechanism. For this purpose, a handle is disposed on the part of the spindle that projects out of the housing, by means of which handle the spindle can be rotated in the circumferential direction. A preferred embodiment provides in that the first control element is used for a slow release of the implant, allowing a high precision in the positioning of the implant to be achieved, rather than using a pushing and retracting of the insertion elements as is the case with the prior art. In an alternative embodiment, the first control element is held stationary relative to the housing during displacement, thereby allowing the release mechanism to be particularly compact in design.

A preferred further development a second actuating element is provided for the relative displacement between the first and second insertion elements, which second actuating element is embodied as separable from the actuator. Thereby, the implant can be released in a structurally simple manner, independently from the actuator. For this purpose, the second control element is preferably connected to an insertion element of the insertion device, and is embodied as a handle. If the insertion device is a catheter, the relevant insertion element can preferably be the outer shaft of the catheter. This connection is effected in a structurally simple manner via the guide element. It can further be advantageous for the second control element to implement a rapid release of the implant, thereby allowing the release mechanism to be used in a particularly variable manner. The two control elements enable easy handling, more particularly, an uncomplicated switching between two release modes. This permits an uncomplicated, simple and rapid regulation of speed during release of the implant. The release of the implant becomes more precise and faster.

It is further proposed that the actuator has at least one track, which is disposed in the direction of the at least second direction of motion. By means of this track, movement in the direction of the at least second direction of motion can be additionally guided, allowing the displacement to be carried out particularly steadily. It is further advantageous for at least one interaction element to be movable along the track in the direction of the at least second direction of motion, thereby allowing the guidance of the tracks to be carried out in a structurally simple manner. The interaction element can be formed by any element deemed appropriate by a person skilled in the art, such as an opening, a groove or an articulated joint. The interaction element is preferably disposed on a leg of the actuator, for example, at one end of the leg. Alternatively or additionally, at least one active element advantageously comprises the interaction element, and particularly preferably, the interaction element is embodied as integral with at least one active element.

According to an advantageous embodiment, the actuator can comprise legs that are articulated to one another, thereby allowing the actuator to be lightweight in structure. It is further advantageous in a preferred embodiment for the legs to be arranged in the form of a parallelogram. As a result, the actuator can be embodied as symmetrical in a structurally simple manner, thereby allowing the movement in the second direction of motion to also be transferred, following a constant displacement principle, to the movement in the first direction of motion. The actuator preferably has four legs, particularly equal in length, which form a type of parallelogram, wherein the spindle lies along an axis of symmetry of the parallelogram.

In an alternative embodiment, it is proposed that the legs are connected via at least one universal joint, which allows the legs to be aligned with one another in a structurally simple and reliable manner. The actuator can thereby be implemented in a cost-effective manner in terms of construction and assembly as having two legs, particularly equal in length, which intersect at a joint. This embodiment allows the legs to be moved opposite one another with a very low risk of tilting.

According to a further aspect of the invention, an insertion device for inserting a medical implant is proposed, which can be released by way of a relative displacement between a first and a second insertion element, and which comprises a release mechanism for releasing the medical implant comprising a body having a proximal end, which is disposed facing toward the operator when in use, and a distal end, which is distant from the operator when in use, wherein between the proximal end and the distal end an actuator is provided, wherein the actuator has a first and at least a second direction of motion for generating a selective relative displacement between the first and second insertion elements of the insertion device, wherein in the first direction of motion, the first and second insertion elements are displaceable relative to one another in the longitudinal direction, and wherein, in the at least second direction of motion, the actuator effects a movement transversely to the longitudinal direction.

With the embodiment according to the invention, an insertion device can be provided, in which strong forces can be easily generated independently of the force to be exerted by the operator or the doctor. In addition, it is easy to handle and has an optimized design. The release of the implant is thereby made more precise and more rapid. Furthermore, the actuator allows the relative displacement to be implemented stably and steadily. All of the above results in a high success rate of implantation. The insertion device can advantageously be a catheter. Particularly advantageously, the insertion device can be used for installing and releasing a prosthesis, a heart valve or a stent.

DESCRIPTION OF THE DRAWINGS

In what follows, the invention will be specified in greater detail, in reference to embodiment examples illustrated in the set of drawings. The drawings show schematic illustrations of.

DETAILED DESCRIPTION

In the figures, elements that are functionally equivalent or act in a similar manner are each identified using the same reference signs. The figures are schematic illustrations of the invention. They do not provide specific parameters for the invention. Moreover, the figures illustrate merely typical embodiments of the invention and are not intended to restrict the invention to the illustrated embodiments.

Figure 1:
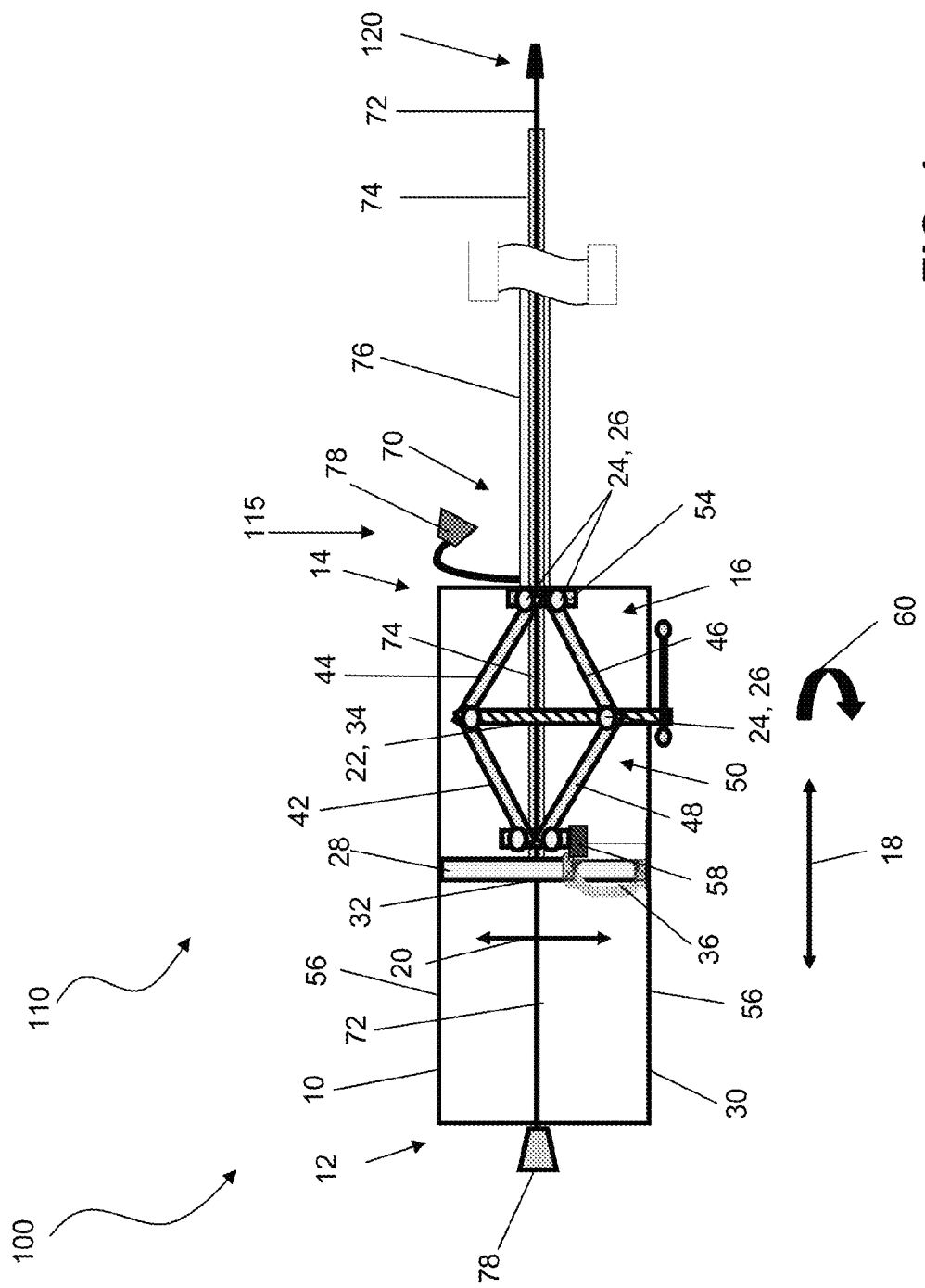
FIG. 1 a cross-section of an advantageous embodiment example of an insertion device and a release mechanism.

FIG. 1 schematically illustrates a side view of an advantageous embodiment example of a release mechanism 100 of an insertion device 110 according to the invention, having a cut-away housing 30, which forms a handle for the insertion device 110.

The insertion device 110 is a catheter, for example, having a shaft region 70 with two coaxially disposed insertion elements 72, 74, for example, an inner shaft (insertion element 72) and an outer shaft (insertion element 74) which encompasses the first, and which can in turn be encompassed by an outer sheath 76. When in use by an operator, in other words when an implant 105 is fastened onto the release mechanism 100 or during an implantation process, the insertion device 110 is oriented with its proximal end 115 facing an operator. The implant 105 is positioned at a distal end 120 of the shaft region 70 between inner shaft and outer shaft, and is to be released at the site of implantation in the animal or human body (see FIG. 2).

The release mechanism 100 is used for releasing the medical implant 105 from the insertion device 110. The implant 105 is disposed at an end 120 of the shaft region 70 that is opposite the housing 30, for example, near a catheter tip. The implant 105 is positioned around the inner insertion element 72, for example, and is released by way of a relative displacement between the first and second insertion elements 72, 74, as is indicated partially in FIGS. 2 and 3. For this purpose, the implant 105 is embodied as self-expanding.

The release mechanism 100 comprises a body 10, embodied as the housing 30, having a proximal end 12, which is disposed toward the operator when in use, and a distal end 14, which is disposed distant from the operator when in use. Between the proximal end and the distal end 12, 14, an actuator 16 is provided. For generating a selective relative displacement between the first and second insertion elements 72, 74 of the insertion device 110, the actuator 16 has a first direction of motion 18 and a second direction of motion 20. In the first direction of motion 18, the first and second insertion elements 72, 74 are displaced relative to one another in the longitudinal direction 18 of the insertion elements 72, 74. In contrast, in the second direction of motion 20, the actuator 16 effects a movement transversely or perpendicularly to the longitudinal direction 18. The actuator 16 is disposed parallel to or not intersecting with the insertion elements 72, 74.

Figure 4:
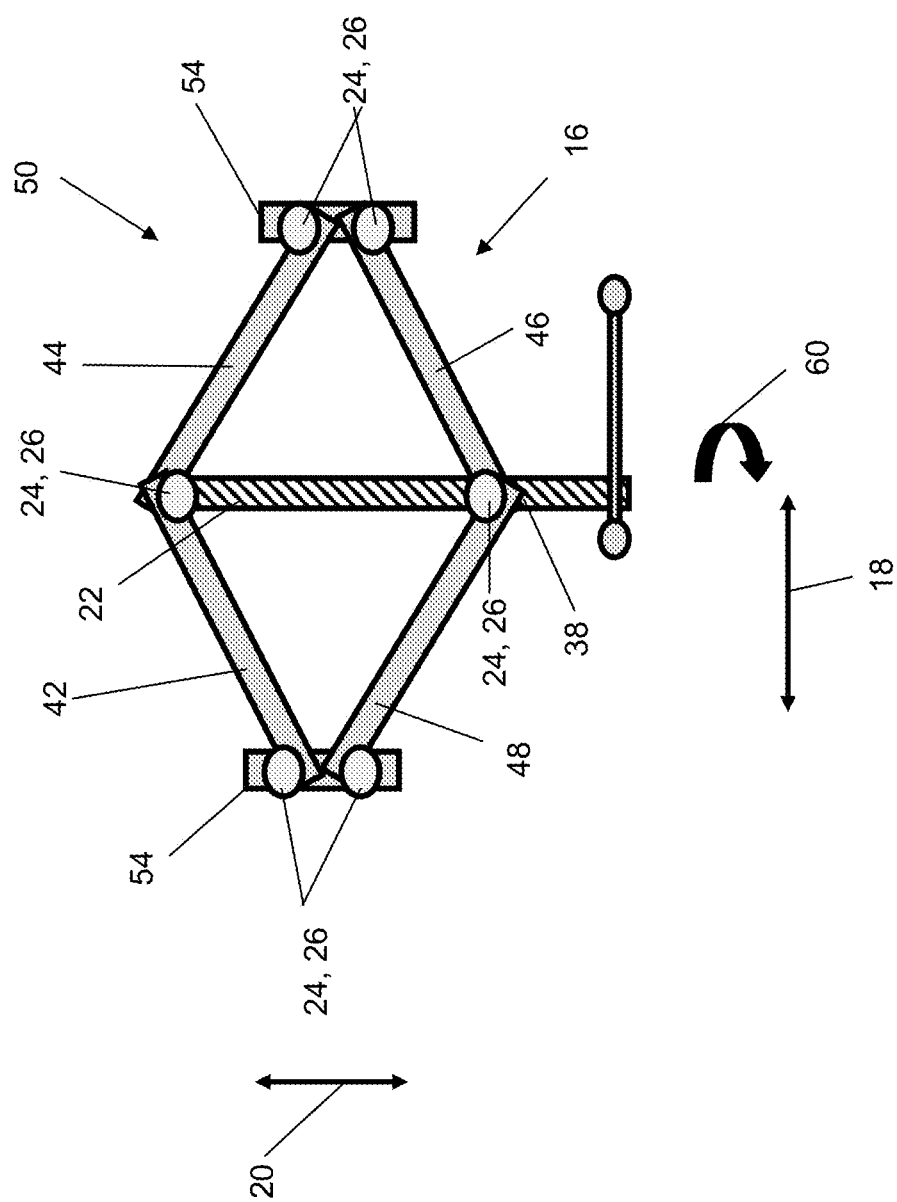
FIG. 4 a detailed illustration of an actuator of the release mechanism of FIG. 1.

In FIG. 4, the actuator 16, which represents a scissor-type mechanism, is illustrated in detail. For conveying movements in the two directions of motion 18, 20, the actuator 16 has four legs 42, 44, 46, 48 of equal length, articulated to one another, which legs are arranged in the form of a parallelogram 50. The actuator 16 further has a plurality of active elements 24, or six, for this purpose, each of which comprises a joint 26. In each case, two legs 42 and 44 or legs 46 and 48 arranged one in front of the other in the longitudinal direction 18 are connected via a joint 26. The pairs of legs 42, 44 and 46, 48 are also arranged axially symmetrically to one another. The two legs 42 and 48 or 44 and 46, each arranged one above the other in the direction 20, perpendicular to the longitudinal direction 18, are connected to one another via a connection element 54, which is disposed parallel to the direction 20. For connecting the respective leg 42, 44, 46, 48 to the respective connection element 54, joints 26 are also provided. Thus, each leg 42, 44, 46, 48 has a joint 26 at each of its opposite ends. The connection element 54 of the actuator 16 that is disposed toward the distal end 14 of the body 10 is attached to the distal end 14 of the body 10 or the housing 30. The connection element 54 of the actuator 16 that is disposed toward the proximal end 12 of the body 10 is detachably connected to a guide element 28 (cf., FIG. 1).

The guide element 28 is embodied as a bar, which spans the housing 30 in the direction 20 and is supported against the housing 30 or is mounted so as to be displaceable in the longitudinal direction 18. For this purpose, the housing 30 has guide devices, not shown here, in its walls 56 that are disposed parallel to the longitudinal direction 18. The insertion element 74 or the outer shaft is fastened on a side of the guide element 28 that is oriented in the direction of the distal end 14 of the body 10. The guide element 28 also has a through passage 32 for the insertion elements 72 or the inner shaft. The shaft is fastened to the proximal end 12 of the body 10 or the housing 30. A lumen of the insertion element 72 (inner shaft) can be vented and/or flushed using a vent valve 78 (also known as a luer lock) disposed at the proximal end 12 of the body. Another vent valve 78 is disposed at the proximal end 115 of the insertion device 110 for venting a lumen of the outer shaft 78. The insertion device 110 further has ventilation holes, not shown here, disposed between the first and second insertion elements 72, 74.

The actuator 16 further has a spindle 22, which is disposed in the direction of the second direction of motion 20, coaxially to the joints 26 of the leg pairs 42, 44 and 46, 48, and which forms an axis of symmetry of the actuator 16. For this purpose, the joints 26 have transfer elements or threaded sections, not shown here, into which a threading of the spindle 22 engages. The spindle 22 further serves as a first actuating element 34, whereby the active elements 24 are coupled to the first actuating element 34. Further, the first actuating element 34 projects out of the housing 30, and on its section that projects out of the housing 30, a rod handle is disposed for the purpose of rotating said element. To detach the connection between the guide element 28 and the actuator 16, a locking element 58 is disposed between these components. The locking element can be actuated, for example, via a second actuating element 36, embodied as a U-type handle, which is connected to the guide element 28.

Figure 2:
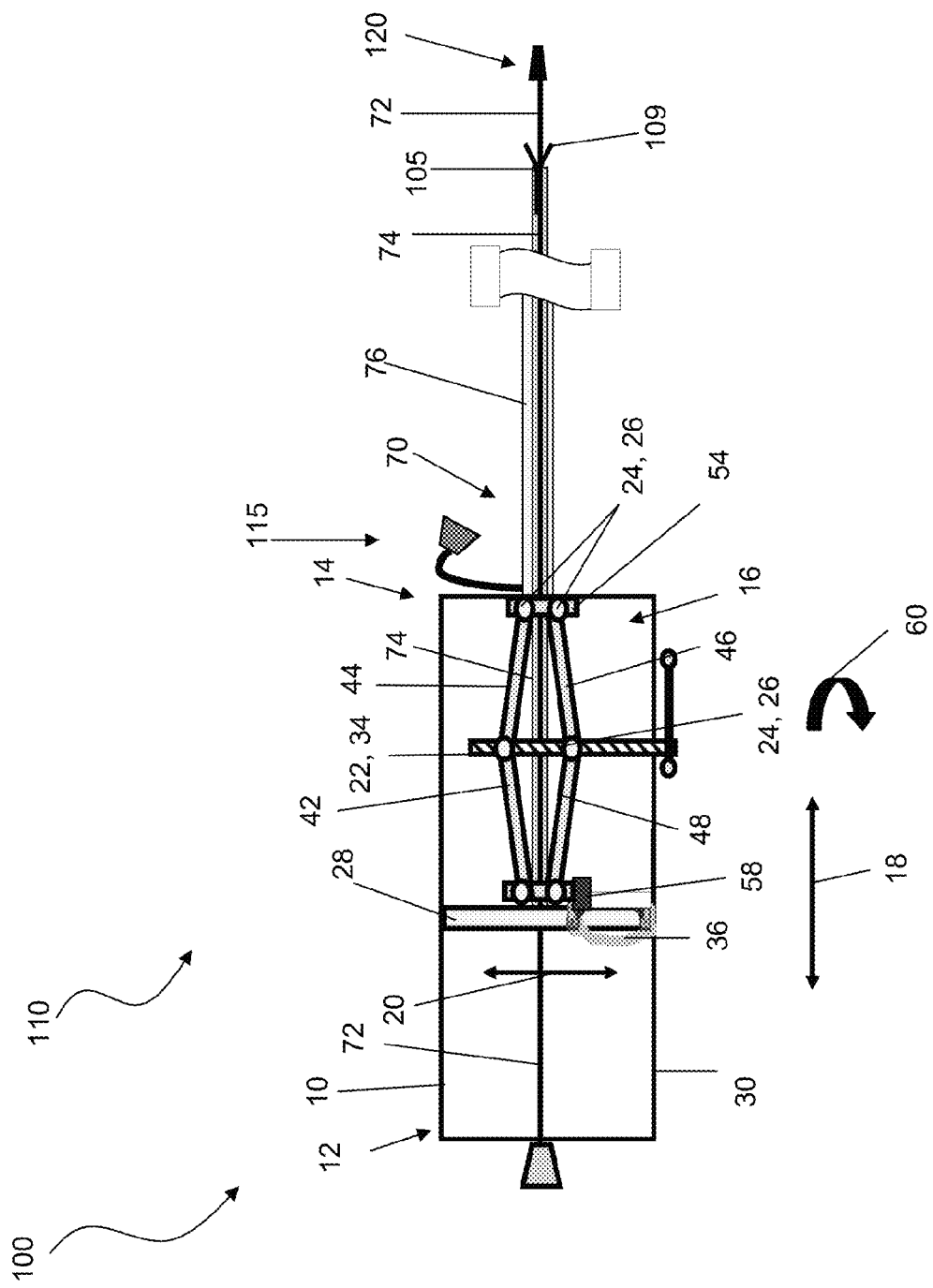
FIG. 2 the insertion device and release mechanism of FIG. 1 during a slow release of an implant via actuation of a first actuating element.

The threading of the spindle 22 and the threading of the threaded sections of the joints 26 are matched to one another in such a way that, when the spindle 22 is rotated in the circumferential direction 60, the joints 26 which connect the pairs of legs 42, 44 and 46, 48 are moved relative to one another in the direction 20, in other words, are movable along the spindle 22. The spindle 22 or an interaction between the spindle 22 and the active elements 24 therefore effects the movement transversely or perpendicularly to the longitudinal direction 18. As is shown in FIG. 2, the parallelogram 50 is thereby compressed in the direction 20, and spread in the longitudinal direction 18. In this, the parallelogram 50 has a range of motion of approx. 25 mm in the direction 20, for example. With this change in shape, the spindle 22 is also displaced in the longitudinal direction 18, for which purpose, the housing 30 has a recess, extending in the longitudinal direction 18 and not illustrated in greater detail, in a region in which the spindle 22 and/or the control element 34 projects out of the housing 30.

Therefore, at the same time that the joints 26 are moving toward one another in the direction 20, the connection elements 54 are moving away from one another in the longitudinal direction 18. Because the actuator 16 is connected to the guide element 28 via the locking element 58, the guide element 28 is also moved or pressed in the direction of the proximal end 12 of the body 10. Because the guide element 28 is mounted on the housing 30, said element guides the actuator 16 during its movement. The movement of the guide element 28 causes a movement of the insertion element 74 in the direction of the proximal end 12 and consequently a release of the implant 105 at the distal end 120 of the insertion device 110. This takes place first at a distal end 109 of the implant 105. The control element 34 is used for a slow release of the implant 105. In principle, the implant 105 can be positioned exclusively via the slow release. For this purpose, the dimensions of the actuator 16 must be adapted to the release geometry of the insertion device and/or to the length of the implant 105. A person skilled in the art will perform this independently on the basis of his knowledge in the field.

Figure 3:
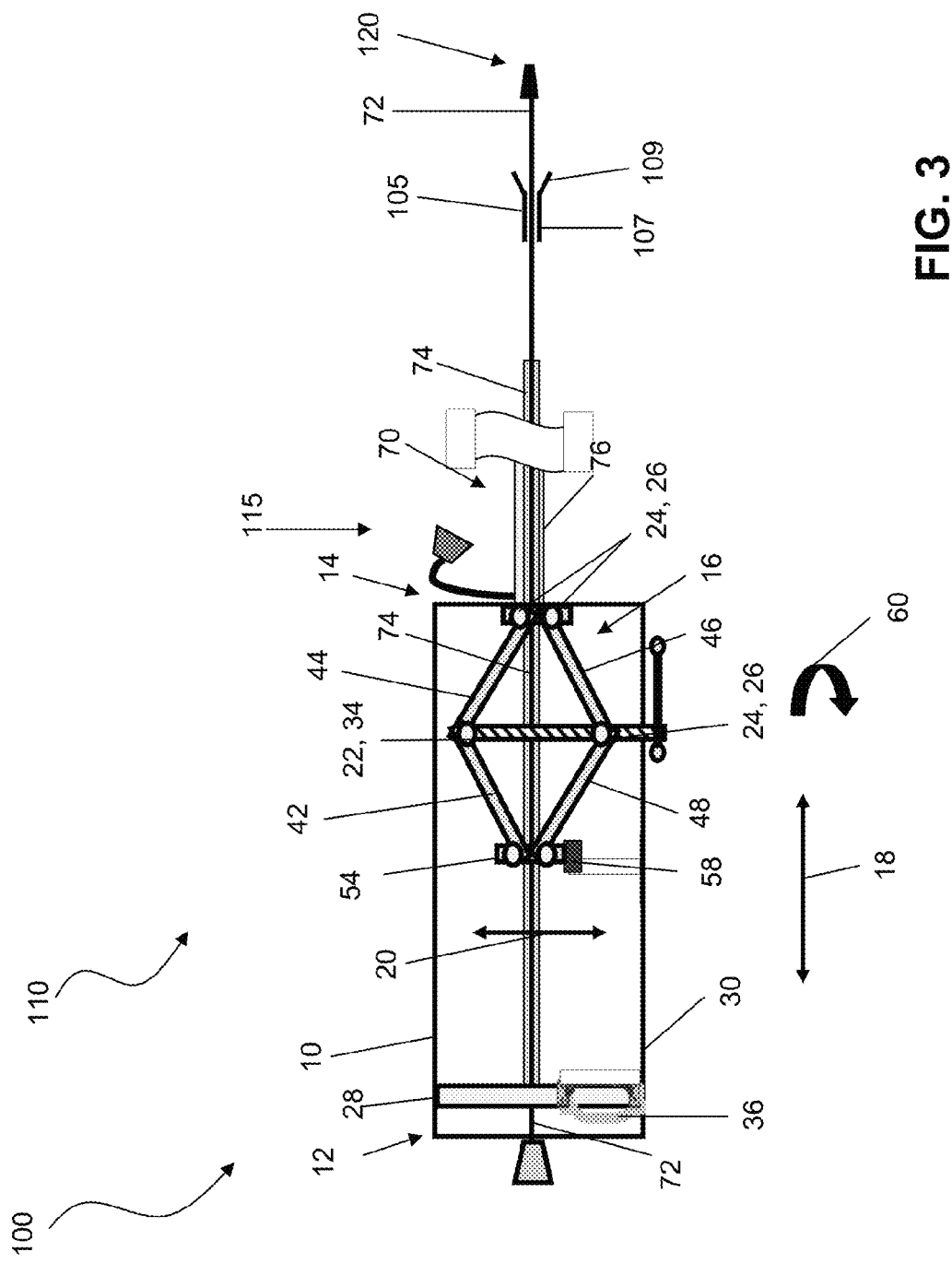
FIG. 3 the insertion device and release mechanism of FIG. 1 during a rapid release of the implant via actuation of a second actuating element.

The second actuating element 36 is used for a rapid release of the implant 105. A rapid release can be carried out following a slow and partial release of the implant 105 for the complete release thereof, or the implant 105 can be emplaced exclusively via the rapid release. By means of the second actuating element 36, the actuator 16 and the guide elements 28 are uncoupled from one another by releasing the locking element 58. Thereafter, the guide device 28 and therefore the insertion element 74 (outer shaft) can be displaced in the longitudinal direction 18 toward the proximal end 12 of the body 10, for example, by manually pulling on the actuating element 36. The proximal end 107 of the implant 105 is also thereby released. This situation is illustrated in FIG. 3. The insertion device 110 is then withdrawn and the implant 105 remains at the site of implantation.

The mechanisms of slow and rapid release, and the components used for these, can also be used for attaching the implant 105 prior to insertion of the insertion device 110 into the body. In this connection, the inner shaft can be released at the distal end 120 as described above. Following positioning of the implant 105 on the inner shaft, the outer shaft can be moved to cover the implant 105 by displacing the guide element 28 in the direction 18 of the distal end 14 of the body 10. A full coverage and movement of the outer shaft in the direction of the distal end 120 can be carried out by means of the actuator 16 once the guide element 28 and the actuator are locked via the locking element 58. In this, the spindle 22 is moved opposite the circumferential direction 60, causing the parallelogram 50 to spread in the direction 20 and to compress in the longitudinal direction 18, thereby moving the guide element 28 and the outer shaft in the direction 18 of the distal ends 14, 120 (not shown).

A length of each body 10 or of the range of motion of the actuator 16 is expediently dimensioned such that said length is at least as long as the length of the implant 105 to be released. In the case of a catheter as the insertion device 110 with a stent as the implant 105, in practice, the stent can initially be released at a slow speed, up to a certain length, and can therefore be very precisely positioned. Afterward, the stent can be fully released at a higher speed. The slow release is particularly well suited to the start of implant release at the implantation site.

Figure 5:
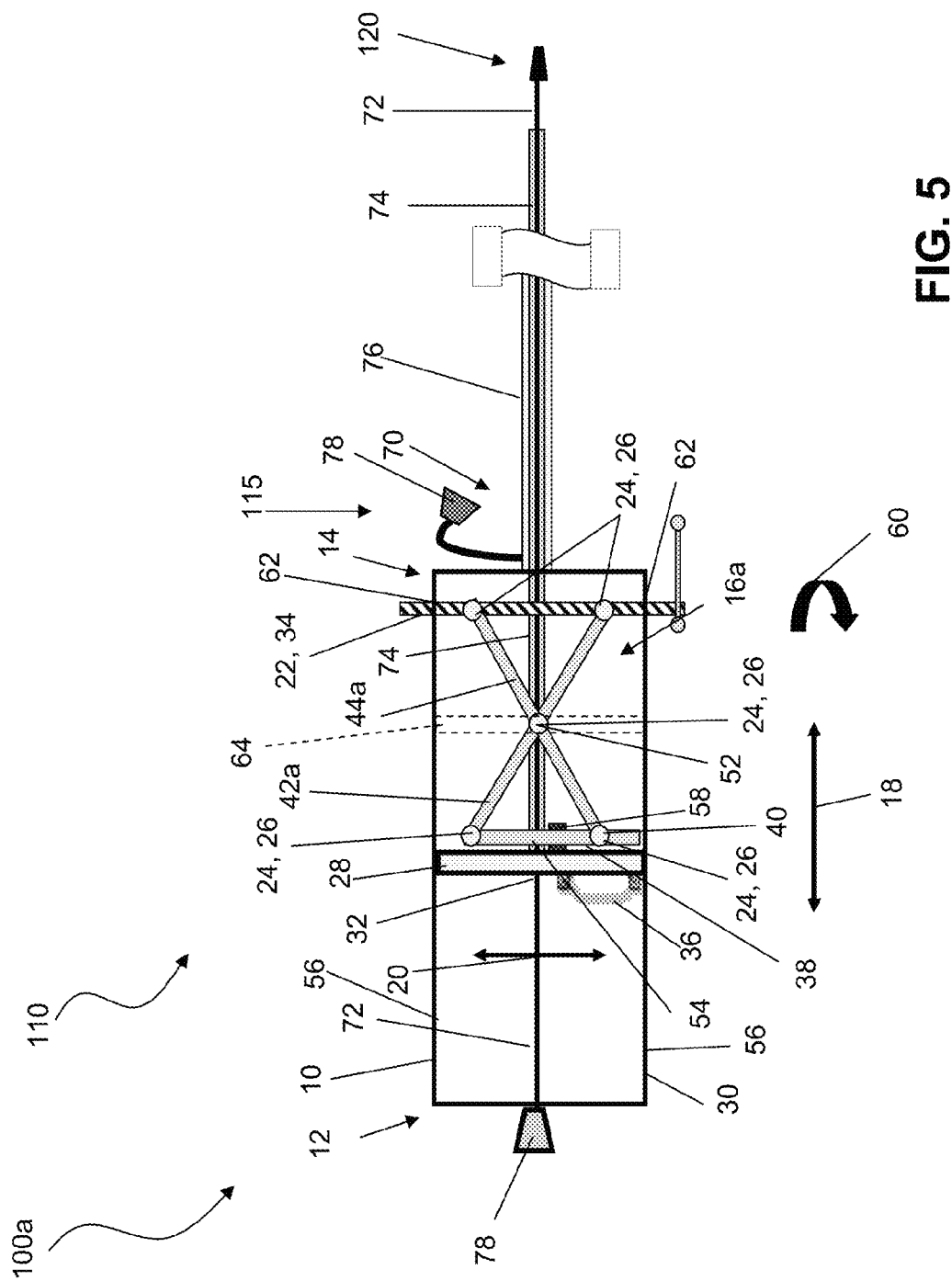
FIG. 5 an alternative release mechanism having an alternative actuator with legs that are connected via a universal joint.

FIG. 5 shows an alternative embodiment example of the release mechanism 100. Essentially, identical components, features and functions are identified by the same reference signs. To distinguish the embodiment example of FIG. 5 from those of FIGS. 1 to 4, however, the letter a is added to the reference signs of the specified components that are different in the embodiment example of FIG. 5. The following description is limited substantially to the differences from the embodiment example in FIGS. 1 to 4, wherein with respect to equivalent components, features and functions, reference may be made to the description of the embodiment example in FIGS. 1 to 4.

FIG. 5 shows an alternative release mechanism 100a having an additional alternative actuator 16a, which is disposed in a body 10, which is formed by a housing 30 and comprises a proximal end 12 and a distal end 14. For generating a selective relative displacement between a first and a second insertion element 72, 74 of an insertion device 110, the actuator 16a comprises a first and a second direction of motion 18; 20, wherein in the first direction of motion 18, the first and second insertion elements 72, 74 can be displaced relative to one another in the longitudinal direction 18, and wherein in the at least second direction of motion 20, the actuator 16a effects a movement transversely to the longitudinal direction 18. For this purpose, the actuator 16a has two legs 42a, 44a of equal length, which are connected via a universal joint 52. The legs 42a, 44a are connected to a spindle 22, at their ends which are disposed in the direction 20 toward the distal end 14 of the body 10, in each case via an active element 24, which comprises a joint 26. For mounting the actuator 16a, the spindle 22, which represents a first control element 34, passes at its two ends through threaded holes 62, not shown in detail, wherein said holes are located in walls 56 of the housing 30 that are oriented in the longitudinal direction 18.

Alternatively, the actuator 16*a* can be supported against the housing 30 via a bearing element 64 on the housing 30, which is guided in guide devices of the housing 30 that are not described in detail.

At the ends of the legs 42*a*, 44*a*, which are disposed in the direction 20 toward the proximal end 12 of the body 10, the legs are connected via a connection element 54 disposed parallel to the spindle 22. For each leg 42*a*, 44*a*, an active element 24, which comprises a joint 26, is provided for this purpose. The connection element 54 and/or the actuator 16*a* comprise a track 38, which is disposed in the direction of the second direction of motion 20 and therefore parallel to the spindle 22. Along the track 38, an interaction element 40 is movable in the direction of the second direction of motion 20. The interaction element 40 is embodied as integral with an active element 24 or a joint 26, whereby the track 38 ensures a movement of at least one active element 24. Additionally, the connection element 54 is detachably fixed to a guide element 28 via a locking element 58. Then, when the spindle 22 is rotated in the circumferential direction 60, the joints 26 at the distal ends of the legs 42*a*, 44*a* move toward one another, thereby pivoting the legs 42*a*, 44*a* around the universal joint 52. The proximal ends of the legs 42*a*, 44*a* are also moved toward one another, and the connection element 54 and the guide element 28 are forced in the direction 18 toward the proximal end 12 of the body 10. The insertion element 74 attached to the guide element 28 is also moved relative to the insertion element 72, thereby slowly releasing an implant or an end, not shown here, at a distal end 120 of the insertion device 110. With this design of the actuator 16*a*, the spindle 22 is held stationary in relation to the housing 30, and does not move in the longitudinal direction 18 with the pivoting movement of the legs 42*a*, 44*a*.

A rapid release is carried out as described in reference to the embodiment example of FIGS. 1 to 4, by means of a second control element 36 with an uncoupling of the actuator 16*a* and the guide element 28.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A release mechanism having two release configurations for releasing a medical implant from an insertion device at two different speeds, in which the implant is released by a relative displacement between a first and a second insertion element, the mechanism comprising:
    a body forming a housing, the body having a proximal end, which is disposed facing toward the operator when in use, and a distal end, which is distant from the operator when in use;
    an actuator positioned between the proximal and distal ends, wherein the actuator has a first direction of motion that extends the actuator longitudinally along the body and at least a second direction of motion that extends the actuator transverse to the direction of the body; and
    a guide element that reversibly locks to the actuator and is fastened to one of the insertion elements;
    wherein a slower release configuration is characterized as providing the actuator locked to the guide element for generating a slower selective relative displacement between the first and second insertion elements of the insertion device in the longitudinal direction, and a faster release configuration is characterized as providing the actuator unlocked from the guide element to permit a faster selective relative displacement between the first and second insertion elements of the insertion device in the longitudinal direction.

2. The release mechanism according to claim 1, wherein the actuator comprises at least one spindle, which is disposed in the direction of the at least second direction of motion, or which effects the extension transversely to the longitudinal direction.

3. The release mechanism according to claim 1, wherein the actuator comprises at least one active element for each of the first and the at least second directions of motion, in order to effect the relative displacement between the first and second insertion elements of the insertion device.

4. The release mechanism according to claim 3, wherein the at least one active element comprises at least one joint.

5. The release mechanism according to claim 2, wherein an interaction between the spindle and at least one active element causes the extension transversely to the longitudinal direction.

6. The release mechanism according to claim 1, wherein the guide element guides the extension of the actuator.

7. The release mechanism according to claim 6, wherein the guide element is supported against the housing.

8. The release mechanism according to claim 6, wherein the guide element comprises a passage for one of the insertion elements.

9. The release mechanism according to claim 1, wherein at least one active element is coupled with a first actuating element, which projects out of the housing, for the slower release of the implant.

10. The release mechanism according to claim 1, wherein a second actuating element releases a locking element that locks the guide element to the actuator thereby converting the release mechanism from the slower release configuration to the faster release configuration.

11. The release mechanism according to claim 3, wherein the actuator has at least one track, which is disposed in the direction of the at least second direction of motion for movement of the at least one interaction element in the direction of the at least second direction of motion.

12. The release mechanism according to claim 1, wherein the actuator comprises legs articulated to one another by joints.

13. The release mechanism according to claim 12, wherein the legs are arranged in the form of a parallelogram.

14. The release mechanism according to claim 12, wherein the legs are connected via at least one universal joint.

15. An insertion device for inserting a medical implant, which can be released by way of a relative displacement between a first and a second insertion element, comprising:
    the release mechanism for releasing the medical implant according to claim 1, wherein the first insertion element is an inner shaft and the second insertion element is an outer shaft; and
    an outer sheath that encompasses the inner and outer shafts.

16. The insertion device according to claim 15, wherein the insertion device is a catheter.

\* \* \* \* \*